(12) United States Patent
Shimada et al.

(10) Patent No.: US 8,763,480 B2
(45) Date of Patent: Jul. 1, 2014

(54) DEW FORMATION TESTING DEVICE AND DEW FORMATION TESTING METHOD

(75) Inventors: Tetsuya Shimada, Osaka (JP); Hirokazu Tanaka, Osaka (JP); Akira Okamoto, Nagaokakyo (JP); Yoshinori Mizuma, Nagaokakyo (JP); Seiichi Okada, Nagaokakyo (JP)

(73) Assignees: Espec Corp. (JP); Murata Manufacturing Co., Ltd. (JP)

( * ) Notice: Subject to any disclaimer, the term of this patent is extended or adjusted under 35 U.S.C. 154(b) by 263 days.

(21) Appl. No.: 13/266,475

(22) PCT Filed: Apr. 5, 2010

(86) PCT No.: PCT/JP2010/002495
§ 371 (c)(1),
(2), (4) Date: Oct. 27, 2011

(87) PCT Pub. No.: WO2010/125748
PCT Pub. Date: Nov. 4, 2010

(65) Prior Publication Data
US 2012/0055273 A1    Mar. 8, 2012

(30) Foreign Application Priority Data
Apr. 28, 2009    (JP) .................................. 2009-109839

(51) Int. Cl.
*G01N 25/68* (2006.01)
*G01N 17/00* (2006.01)
(52) U.S. Cl.
USPC ............................................ 73/865.6; 73/73

(58) Field of Classification Search
USPC .............................................. 73/73, 77, 865.6
See application file for complete search history.

(56) References Cited

U.S. PATENT DOCUMENTS

| | | | | |
|---|---|---|---|---|
| H000229 H | * | 3/1987 | Phillips ........................... | 165/96 |
| 4,817,447 A | * | 4/1989 | Kashima et al. ............. | 73/865.6 |

(Continued)

FOREIGN PATENT DOCUMENTS

| | | | | |
|---|---|---|---|---|
| JP | 4-29311 | 9/1988 | | |
| JP | 63309846 A | * 12/1988 | ............. | G01N 25/68 |

(Continued)

OTHER PUBLICATIONS

WIPO Written Report for PCT/JP1010/002495 Nov. 17, 2011.*

*Primary Examiner* — Lisa Caputo
*Assistant Examiner* — Punam Roy
(74) *Attorney, Agent, or Firm* — Gerald E. Hespos; Michael J. Porco; Matthew T. Hespos

(57) ABSTRACT

A dew formation testing device has an adjustment tank capable of adjusting the temperature and humidity of air to predetermined temperature and humidity, a testing tank installed separately from the adjustment tank and having a sample base that has a mounting surface, onto which a testing sample W can be placed, and that is capable to cool the mounting surface, and ducts that link the adjustment unit and the testing tank. The testing tank is provided with an air guide member that, when air flowing into the testing tank through the duct flows onto the sample base from a side of the sample base, guides the air in the direction tilted downward at a predetermined angle, the guidance being performed at a position right above the sample base at an end thereof which is on the upstream side of the air flow.

12 Claims, 15 Drawing Sheets

(56) References Cited

U.S. PATENT DOCUMENTS

| | | | |
|---|---|---|---|
| 4,995,273 A * | 2/1991 | Kisima et al. | 73/865.6 |
| 5,052,818 A * | 10/1991 | Nishizawa et al. | 374/17 |
| 5,537,868 A * | 7/1996 | Shofner et al. | 73/160 |
| 5,692,556 A | 12/1997 | Hafner | |
| 7,135,877 B2 * | 11/2006 | Beaman et al. | 324/750.09 |
| 7,765,868 B2 * | 8/2010 | Pirsch et al. | 73/431 |
| 8,359,906 B2 * | 1/2013 | Shimada et al. | 73/77 |

FOREIGN PATENT DOCUMENTS

| | | | | |
|---|---|---|---|---|
| JP | 5-164684 | | 6/1993 | |
| JP | 06058891 A | * | 3/1994 | ............ G01N 25/68 |
| JP | 7-27374 | | 1/1995 | |
| JP | 09-210897 | | 8/1997 | |
| JP | 10-78387 | | 3/1998 | |
| JP | 3113823 | | 12/2000 | |
| JP | 2003-130399 | | 5/2003 | |
| JP | 2007-271551 | | 10/2007 | |

* cited by examiner

UPSTREAM
OF THE AIR FLOW

DOWNSTREAM
OF THE AIR FLOW

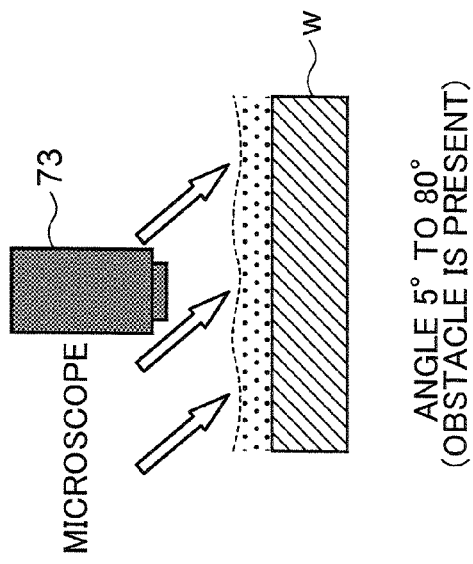
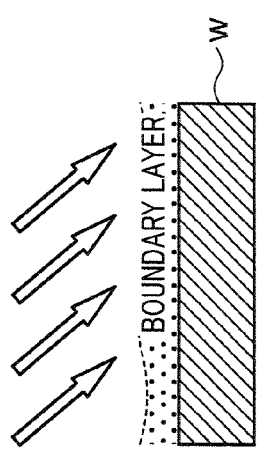
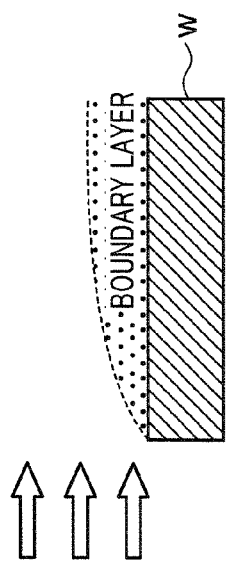

IMMEDIATELY AFTER
OCCURRENCE OF
DEW FORMATION

AFTER 10 MIN SINCE
THE OCCURRENCE

DEW FORMATION TESTING DEVICE AND DEW FORMATION TESTING METHOD

BACKGROUND OF THE INVENTION

1. Field of the Invention

The present invention relates to a dew formation testing device and a dew formation testing method.

2. Description of the Related Art

Dew formation testing devices that can perform dew formation testing have been known, as described in JP 2007-271551, JP 3113823 and JP 5-164684.

The dew formation testing device disclosed in JP 2007-271551 has a full-body tank constituted by thermally insulating panels. A testing chamber, a low-temperature adjustment tank, and a high-temperature adjustment tank are included in the full-body tank. The low-temperature adjustment tank is provided below the testing chamber, and low-temperature and low-humidity air is generated in the low-temperature adjustment tank. An introducing port damper and a discharge port damper for performing/stopping the circulation of the air between the testing chamber and the low-temperature adjustment tank are provided in the floor panel of the testing chamber. The high-temperature adjustment tank is provided at a back surface side of the testing chamber and generates high-temperature and high-humidity air. An introducing port damper and a discharge port damper for performing/stopping the circulation of the air between the testing chamber and the high-temperature adjustment tank are provided in the back panel of the testing chamber. In the dew formation testing device, the interior of the testing chamber is adjusted to the condensation environment by adjusting the timing for introducing the air generated in each adjustment tank into the testing chamber.

The dew formation environment testing device disclosed in JP 3113823 has a device main body. The interior of the device main body is partitioned into an air conditioning chamber and a testing chamber by a partition plate. A humidifier, an evaporator, and a heater are provided in the air conditioning chamber, and a cooler is provided at a sample base of the testing chamber. An introducing port for introducing, into the air conditioning chamber, the air adjusted to the predetermined temperature and humidity in the air conditioning chamber and a discharge port for returning the air from the testing chamber into the air conditioning chamber are provided in the partition plate. In such a dew formation environment testing device, dew formation can be generated on a testing sample located on the sample base by controlling the humidifier and the cooler and also controlling the evaporator and the heater with a dew formation controller.

Further, in the dew formation testing device disclosed in JP 5-164684, the interior of the device main body is partitioned into a testing chamber and an air conditioning chamber. A constant dew point generation device and a cold air flow generator are provided inside the device main body. The humid air generated in the constant dew point generation device and the low-temperature air generated in the cold air flow generator are introduced by ducts into the testing chamber. As a result, dew formation can be generated on the testing sample placed on the sample base inside the testing chamber.

In the testing devices described in JP 2007-271551 and JP 3113823, the air circulates between the testing chamber and the air conditioning chamber (or the adjustment tank). However, in such testing devices, it is difficult to control accurately the flow of air inside the testing chamber and therefore the dew formation on the testing sample is difficult to maintain in a substantially uniform state.

In the testing device described in JP 5-164684, the air with adjusted temperature and humidity flows inside the duct and is guided on the sample base located inside the testing chamber. Therefore, the air that has flown through the duct can directly fall on the testing sample. For this reason, the temperature of the testing sample can be made lower than the temperature of the entire testing chamber and dew formation can be generated on the testing sample. However, since the outlet port of the duct is positioned right above the testing sample, water of condensation generated inside the duct can fall on the testing sample. As a result, it is difficult to maintain the dew formation on the testing sample in a substantially uniform state.

Further, all of the testing devices described in JP 2007-271551, JP 3113823 and JP 5-164684 have a configuration in which the testing chamber is formed integrally with the air conditioning chamber. Therefore, vibrations of the air conditioning chamber are transmitted to the testing chamber. As a result, condensation droplets are caused to merge or flow, thereby affecting the condensation state on the testing sample. Because the testing sample is thus affected by vibrations, it is also difficult to maintain a substantially uniform state of dew formation on the testing sample.

SUMMARY OF THE INVENTION

It is an object of the present invention to provide a dew formation testing device and a dew formation testing method that make it possible to maintain a substantially uniform state of dew formation on a testing sample.

A dew formation testing device according to one aspect of the present invention is a device for performing dew formation testing, this device including: an adjustment unit capable of adjusting temperature and humidity of air to predetermined temperature and humidity; a testing tank installed separately from the adjustment unit and provided with a sample base that has a mounting surface, onto which a testing sample can be placed, and that is capable to cool the mounting surface; and a duct linking the adjustment unit and the testing tank, wherein the testing tank is provided with an air guide member that, when air flowing into the testing tank through the duct flows onto the sample base from a side of the sample base, guides the air in a direction tilted downward at a predetermined angle, the guidance being performed at a position right above the sample base at an end thereof which is on the upstream side of the air flow.

A dew formation testing method according to another aspect of the present invention is a method for performing dew formation testing, this method including: adjusting temperature and humidity of air to predetermined temperature and humidity inside an adjustment unit; introducing the air from the adjustment unit into a testing tank through a duct; cooling a mounting surface of a sample base, onto which a testing sample has been placed, inside the testing tank; and guiding the air from a side of the sample base in a direction tilted downward at a predetermined angle, with the guidance being performed at a position right above the sample base at an end thereof which is on the upstream side of the air flow, and causing the air to flow on the sample base, thereby causing dew formation on the testing sample.

BRIEF DESCRIPTION OF THE DRAWINGS

FIGS. 5A, 5B, and 5C illustrate the effect of a boundary layer in relation to the air flow direction.

DETAILED DESCRIPTION OF THE PREFERRED EMBODIMENTS

Embodiments of the present invention will be explained below with reference to the appended drawings.

First Embodiment

Figure 1:
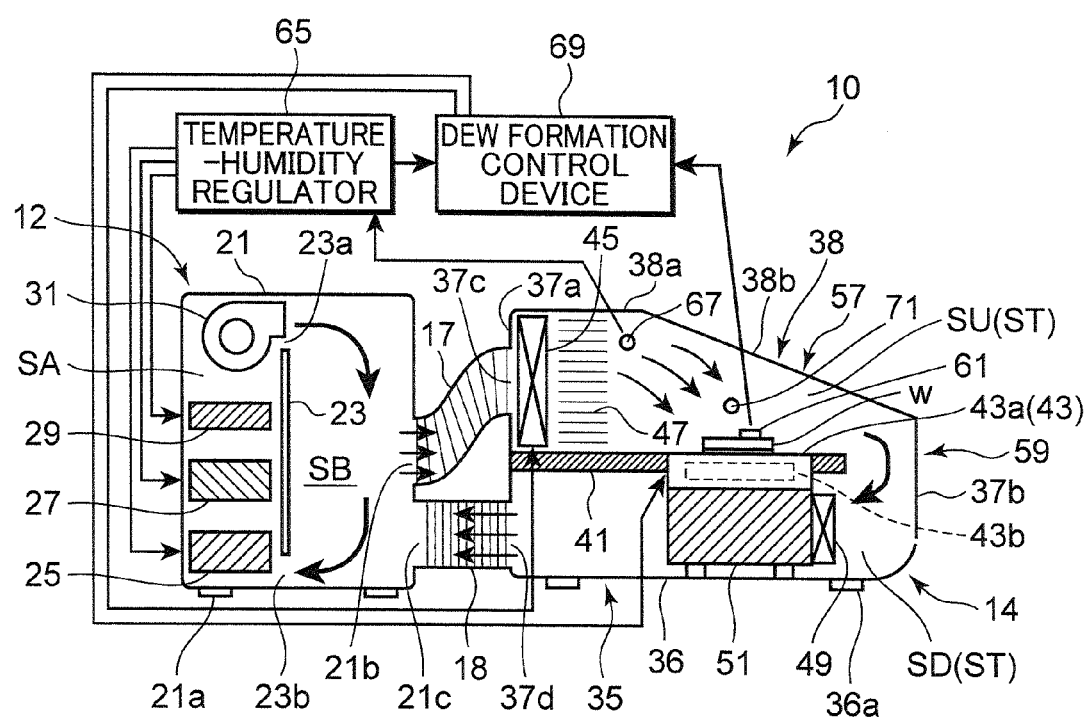
FIG. 1 illustrates schematically the dew formation testing device according to the first embodiment of the present invention.

As shown in FIG. 1, a dew formation testing device 10 according to the first embodiment is provided with an adjustment tank 12 as an example of an adjusting unit, a testing tank 14, and ducts 17, 18 connecting the tanks.

The adjustment tank 12 is a section for adjusting the temperature and humidity of air supplied into the testing tank 14 to predetermined temperature and humidity. The adjustment tank 12 is provided with a hollow casing 21. Legs 21a are provided at the bottom of the casing 21, and the legs 21a are grounded.

A partition plate 23 is disposed so as to extend vertically inside the casing 21, and the adjustment tank 12 is partitioned by the partition plate 23 into an adjustment space SA and a buffer space SB. Two communication holes 23a, 23b are provided in the partition plate 23. One communication hole 23a is positioned in the upper end portion of the partition plate 23, and the other communication hole 23b is positioned in the lower end portion of the partition plate 23.

A humidifier 25, a cooler 27, a heater 29, and an air blower 31 are provided in the adjustment space SA. The air blower 31 is provided in the upper end portion of the adjustment space SA and blows the air with adjusted temperature and humidity into the buffer space SB. As a result, the air circulates inside the adjustment tank 12 between the adjustment space SA and the buffer space SB through the upper communication hole 23a and the lower communication hole 23b. The air blower 31 may have a variable air blowing capacity or a constant air blowing capacity.

Nothing is provided in the buffer space SB. The air from the communication hole 23a located in the upper end portion of the buffer space SB flows thereinto. The air located inside the buffer space SB flows out from the communication hole 23b located in the lower end portion of the buffer space SB and returns to the adjustment space SA. The air flows inside the buffer space SB, but the pressure inside the buffer space SB is substantially stable. An outflow port 21b and an inflow port 21c are formed at positions facing to the buffer space SB in the side wall of the casing 21. The outflow port 21b is positioned below the upper communication hole 23a formed in the partition plate 23, and the inflow port 21c is positioned below the outflow port 21b.

The testing tank 14 is a section for performing dew formation test of a testing sample W. The testing tank 14 is provided with a hollow casing 35. The casing 35 of the testing tank 14 is provided with a bottom 36 formed, for example, in a rectangular shape, side walls 37a, 37b provided so as to rise vertically from the edge of the bottom 36, and a ceiling 38 provided so as to bridge the upper end portions of the side walls 37a, 37b.

An introducing port 37c for introducing air into the casing 35 and a lead-out port 37d for discharging the air located inside the casing 35 are formed in one side wall (side wall on the left side in FIG. 1) 37a. The introducing port 37c is positioned above the lead-out port 37d. An upstream duct 17 leading from the introducing port 37c to the outflow port 21b of the adjustment tank 12 is connected to the side wall 37a. Further, a downstream duct 18 leading from the lead-out port 37d to the inflow port 21c of the adjustment tank 12 is connected to the side wall 37a. As a result, the air located inside the buffer space SB is introduced into the testing tank 14 through the upstream duct 17, and the air located inside the testing tank 14 is returned into the buffer space SB through the downstream duct 18. The upstream duct 17 for example has a length of about 1.5 m to 2 m.

The introducing port 37c of the testing tank 14 is positioned above the outflow port 21b of the adjustment tank 12. In other words, the upstream end of the upstream duct 17 is provided at a position lower than the downstream end of the upstream duct 17. Therefore, the air flowing in the upstream duct 17 flows upward, and when this air condensates inside the duct 17, the water of condensation flows through the duct 17 toward the adjustment tank 12. Further, water particles generated by the humidifier 25 and floating in the air are caused by the inertia force to adhere to the wall surface of the duct 17, but these water particles merge with the water of condensation and also flow toward the adjustment tank 12. Therefore, the water of condensation can be prevented from flowing into the testing tank 14.

Legs 36a are provided at the bottom 36 of the casing 35, and the legs 36a are grounded. Thus, the testing tank 14 and the adjustment tank 12 are installed separately from each other. The testing tank 14 and the adjustment tank 12 are connected together by ducts 17, 18. Therefore, vibrations of the adjustment tank 12 are unlikely to be transmitted to the testing tank 14.

The interior of the testing tank 14 is formed as a testing space ST. A partition member 41, a sample base 43, a first fan 45, a flow adjusting plate 47, a second fan 49, and fins 51 are provided inside the testing tank 14. The partition member 41 is a plate-shaped member provided in a posture that extends from the side wall 37a having the introducing port 37c and the lead-out port 37d toward the opposing side wall 37b at a height between the introducing port 37c and the lead-out port 37d. A gap of a predetermined width is formed between the partition member 41 and the opposing side wall 37b, and an upstream space SU located above the partition member 41 communicates with a downstream space SD located below the partition member 41 via this gap. The air from the adjustment tank 12 is introduced into the upstream space SU through the introducing port 37c. The air of the downstream space SD is discharged through the lead-out port 37d, and this air is returned to the adjustment tank 12. A configuration may be also used in which the downstream duct 18 is omitted and the air discharged from the lead-out port 37d of the testing tank 14 is discharged to the outside and not returned to the adjustment tank 12.

An opening is formed in the partition member 41, and the sample base 43 is inserted from below into the opening. A mounting surface 43a, which is the upper surface of the sample base 43, is horizontal and faces the upstream space SU of the testing space ST. The sample base 43 is constituted by a material with a high thermal conductivity, but since the gap is formed between the sample base 43 and the partition member 41, heat from the sample base 43 is unlikely to be transferred to the partition member 41.

The sample base 43 is provided with a heating-cooling unit 43b including a Peltier element and configured so that the mounting surface 43a can be heated or cooled by the heating-cooling unit 43b. Thus, the sample base 43 functions as a heating-cooling plate that heats or cools the testing sample W located on the mounting surface 43a. A large number of fins 51 are thermally connected to the heating-cooling unit 43b, and these fins 51 are provided in the downstream space SD. As a result, the air passing through the upstream space SU flows through between the fins 51. Thus, when the Peltier element of the heating-cooling unit 43b functions to cool the mounting surface 43a of the sample base 43, the air located inside the downstream space SD is heated by the fins 51 to which the heat of the heat-emitting section of the Peltier element is transferred.

The first fan 45 is provided in the upstream space SU. More specifically, the first fan 45 is provided immediately inside the introducing port 37c in the interior of the testing tank 14. The first fan 45 is configured by a fan with a variable air blowing capacity.

The configuration in which the first fan 45 is provided inside the upstream space SU positioned downstream of the upstream duct 17 is not limiting. For example, the first fan 45 may be also provided in the buffer space SB which is located upstream of the upstream duct 17 (see FIG. 11). In this case, the first fan 45 is provided so as to cover the outflow port 21b of the adjustment tank 12. In the case of the configuration in which the first fan 45 is disposed in the adjustment tank 12, vibrations of the first fan 45 can be prevented from being transmitted to the sample base 43. Therefore, vibrations of the sample base 43 can be inhibited more effectively. The first fan 45 may be also provided at the intermediate position of the upstream duct 17.

The flow adjusting plate 47 is provided immediately downstream of the first fan 45 and adjusts the flow of air blown out from the first fan 45. The flow adjusting plate 47 is positioned upstream of the below-described air guide member 57.

The second fan 49 is provided immediately upstream of the fins 51. The second fan 49 sucks in the air located inside the upstream space SU and blows out this sucked-in air toward the fins 51. Thus, the air located inside the upstream space SU is cooled by the sample base 43 (or the testing sample W), but this air is heated inside the downstream space SD. As a result, dew formation inside the downstream space SD can be inhibited. Further, the second fan 49 may be also disposed in the interior of the adjustment tank 12 or at an intermediate position of the downstream duct 18 (see FIG. 11).

A thermal resistance reducing material 55 (see FIG. 2) is provided at the mounting surface 43a of the sample base 43. The mounting surface 43a of the sample base 43 is thermally connected to the testing sample W by this thermal resistance reducing material 55. The thermal resistance reducing material 55 is constituted, for example, by a thermally conductive sheet or thermally conductive grease. Thus, GR-b manufactured by Fuji Polymer industries co., LTD. is an example of the thermally conductive sheet, and G-747 manufactured by Shin-Etsu Chemical Co., Ltd is an example of the thermally conductive grease. Where the zone (exposed portion) of the mounting surface 43a where the testing sample W is not located is protected as appropriate by a thermally insulating material or the like, the occurrence of unnecessary heat dissipation from the Peltier element or unnecessary dew formation can be prevented.

Part of the ceiling 38 of the casing 35 of the testing tank 14 functions as the air guide member 57. Thus, the ceiling 38 has a horizontal portion 38a extending horizontally from the upper end portion of the side wall 37a connected to the ducts 17, 18 and a tilted portion 38b extending obliquely downward from the distal end of the horizontal portion 38a. This tilted portion 38b has a width larger than at least the width of the sample base 43 in the direction of air flow and extends from a position on the upstream side of the air flow (side close to the introducing port 37c) from the end (left end in FIG. 1) of the sample base 43 on the upstream side of the air flow to the position on the downstream side of the air flow from the end of the sample base 43 on the downstream side of the air flow. The lower surface (inner surface) of the tilted portion 38b is a flat tilted surface that descends gradually from the upstream side of the air flow to the downstream side of the air flow. Thus, when the air flows from a side of the sample base 43 to above the sample base 43 inside the upstream space SU, the tilted portion 38b guides the air in the direction tilted downward at a predetermined angle, the guidance being performed at a position just above the sample base 43 at the end thereof which is on the upstream side of the air flow. Therefore, the tilted portion 38b functions as the air guide member 57. The gap between the tilted portion 38b of the casing 35 and the partition member 41 and sample base 43 gradually narrows from the upstream side of the air flow to the downstream side of the air flow. Thus, the area of the flow passage of air inside the upstream space SU is gradually reduced by the air guide member 57 from the upstream side of the air flow to the downstream side of the air flow.

The lower end (right end in FIG. 1) of the tilted portion 38b is formed integrally with the side wall (opposing side wall) 37b of the casing 35. A lid 59 constituted by the tilted portion 38b and the opposing side wall 37b is configured to be rotatable about a connection site thereof with the horizontal portion 38a as an axis (rotation axis). The lid 59 can open the testing space ST when the testing sample W is introduced or taken out.

The testing tank 14 is provided with a dew formation amount sensor 61 which is an example of a dew formation detection unit that can detect dew formation occurring on the surface of the testing sample W. The dew formation amount sensor 61 is provided with comb-shaped electrodes and outputs a signal with a generation frequency corresponding to the electrostatic capacitance between the electrodes. Thus, where the dew formation amount between the electrodes changes, the electrostatic capacitance between the electrodes also changes. Therefore, the dew formation amount sensor 61 changes the generation frequency according to the variations in the electrostatic capacitance. The dew formation amount sensor 61 can thus detect the dew formation amount.

The dew formation amount sensor 61 may be thermally connected to the testing sample W by means of the thermal resistance reducing material 63 (see FIG. 2) such as a thermally conductive sheet or thermally conductive grease or may be in direct contact with the testing sample W.

The dew formation testing device 10 is provided with a temperature-humidity regulator 65 that controls the humidifier 25, the cooler 27, and the heater 29. The temperature-humidity regulator 65 inputs the signal outputted from a temperature-humidity sensor 67 provided in the upstream space SU. Further, the temperature-humidity regulator 65 can set the temperature and humidity inside the testing tank 14. The temperature-humidity regulator 65 controls the humidifier 25, the cooler 27, and the heater 29 on the basis of signals from the temperature-humidity sensor 67 so as to obtain the temperature and humidity that have been set. The temperature-humidity sensor 67 is provided inside the upstream space SU in a location where the temperature-humidity sensor 67 is unlikely to be affected by heat of the sample base 43.

The dew formation testing device 10 is provided with a dew formation control device 69 that controls the air blowing amount of the first fan 45 and heating-cooling amount of the sample base 43. The dew formation control device 69 controls the first fan 45 and the heating-cooling unit 43b on the basis of signals outputted from the dew formation amount sensor 61, so that a predetermined amount of dew formation is generated on the testing sample W.

Figure 2:
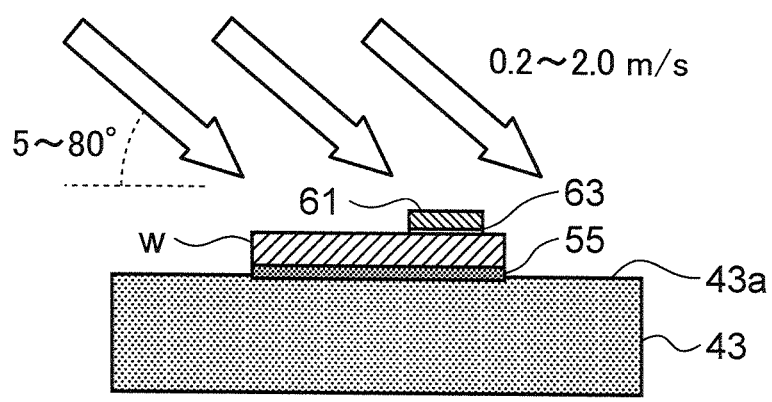
FIG. 2 illustrates the flow of air toward the testing sample in the dew formation testing device.
Figure 3:
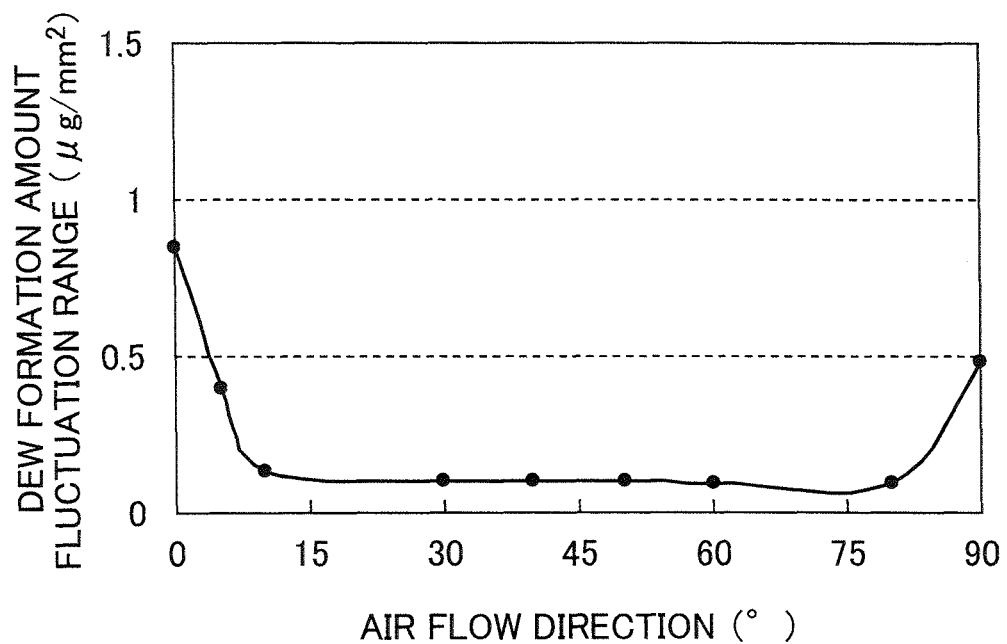
FIG. 3 illustrates the relationship (an example) between the air flow direction and the fluctuation width of dew formation amount.

The tilting angle of the tilted portion 38b is preferably equal to or greater than 5 degrees, more preferably equal to or greater than 10 degrees, and equal to or less than 80 degrees with respect to the horizontal direction. In this case, as shown in FIG. 2, the air flowing toward the testing sample W flows downward at a tilting angle of 5 degrees to 80 degrees (more preferably 10 degrees to 80 degrees, even more preferably 10 degrees to 30 degrees). When the inclination of the air flow direction is less than 5 degrees or more than 80 degrees with respect to the horizontal direction, as shown in FIG. 3, the fluctuation range of the dew formation amount on the surface of the testing sample W increases. In other words, the dew formation amount related to the predetermined surface area fluctuates. Therefore, the fluctuation range of dew formation amount can be inhibited by setting the air flow direction to 5 degrees to 80 degrees (more preferably 10 degrees to 80 degrees, even more preferably 10 degrees to 30 degrees). FIG. 3 shows an example of results obtained at an air flow velocity of 0.5 m/s.

Figure 4A:
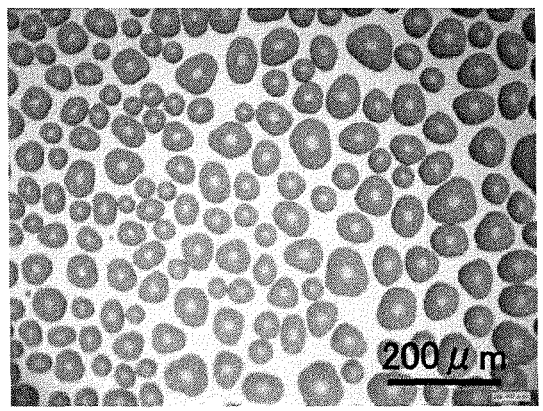
FIG. 4A shows dew formation on the surface of the testing sample on the upstream side of the air flow.
Figure 4B:
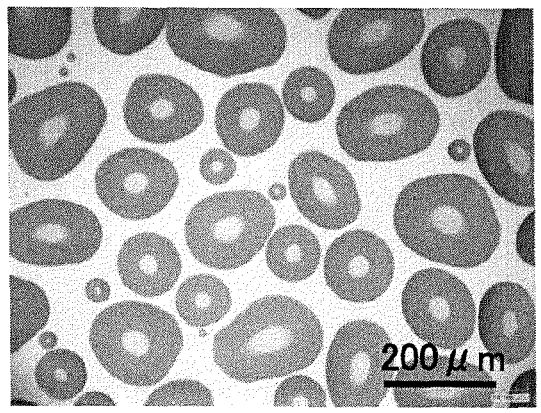
FIG. 4B shows dew formation on the surface of the testing sample on the downstream side of the air flow.

When the air flow direction is at 0 degree, the particle size of dew differs significantly between the upstream side of the air flow and the downstream side of the air flow as shown in FIGS. 4A and 4B. The following explanation can be suggested for this effect. As shown in FIG. 5A, in the below-described air flow velocity region, a layer in which the air does not flow (boundary layer) is formed such that the thickness of the boundary layer increases with a transition toward the downstream side of the air flow, and difference in heat exchange amount occurs between the upstream side of the air flow and the downstream side of the air flow. Where the air flow direction is at 5 degrees to 80 degrees, the thickness of the boundary layer is practically the same on the upstream side of the air flow and the downstream side of the air flow (FIGS. 5B and 5C). The same result is obtained when an obstacle, such as the below-described microscope, is present (FIG. 5C). FIGS. 4A and 4B are photos illustrating dew formation on the surface of the testing sample W. FIG. 4A shows dew formation occurring at a location on the upstream side of the air flow and FIG. 4B shows dew formation occurring at a location on the downstream side of the air flow.

Figure 6A:
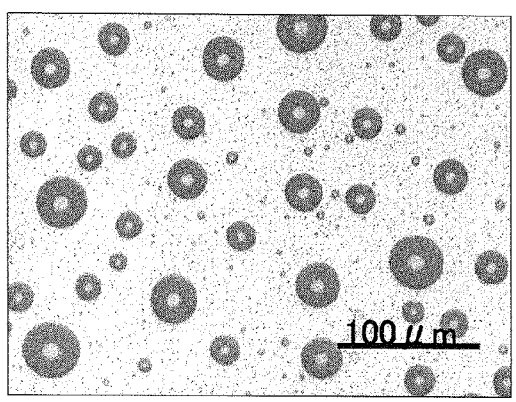
FIGS. 6A and 6B illustrate variations in the dew formation state with time in the case where the air flow velocity is less than 0.2 m/s.
Figure 6B:
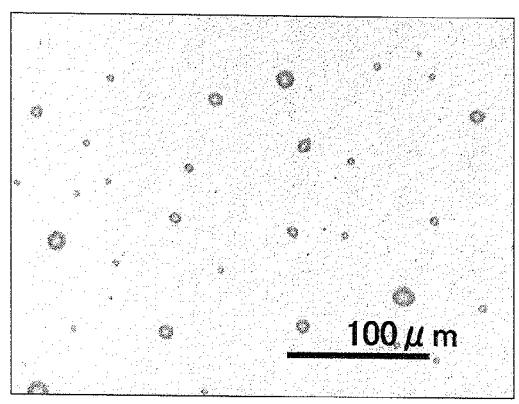

The air flow velocity at a position just above the testing sample W is preferably equal to or higher than 0.2 m/s and less than 2.0 m/s. When the air flow velocity is less than 0.2 m/s, air circulation on the surface of the testing sample W becomes insufficient and the amount of moisture supplied from the air to the testing sample W tends to decreases. Therefore, the system becomes highly sensitive to a slight movement of air and the state of environment such as radiation and light. FIGS. 6A and 6B show the state immediately after the occurrence of dew formation after the first fan 45 has been stopped (air flow velocity 0 m/s) (FIG. 6A) and the state after 10 min has elapsed (FIG. 6B). Therefore, in order to stabilize the dew formation on the testing sample W over a predetermined time interval, it is preferred that the air flow velocity be equal to or greater than 0.2 m/s.

Figure 7:
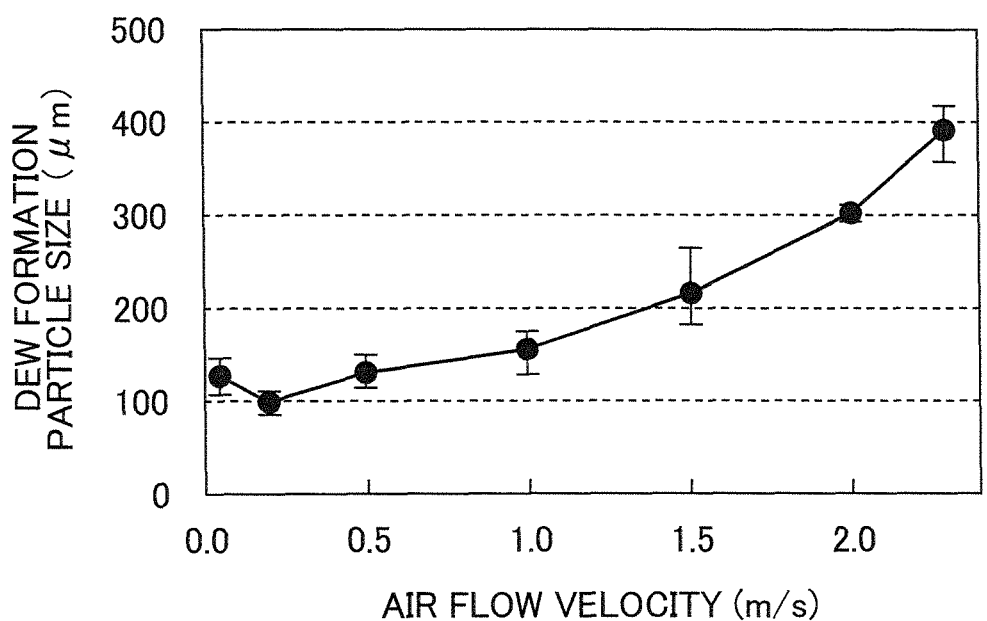
FIG. 7 is a characteristic diagram illustrating the relationship between the air flow velocity and the spread of particle size of dew formation (an example of results obtained in the case where the angle is 5 degrees).

FIG. 7 shows an example of results obtained when the air flow direction angle is 5 degrees and the dew formation amount set value is 10 µg/mm$^2$. As shown in FIG. 7, when the air flow velocity is 0.2 m/s, the dew formation particle size is at a minimum and the variability thereof is also at a minimum. Where the air flow velocity is less than 0.2 m/s, the dew formation particle size increases and the variability thereof also increases. When the air flow velocity is 0 m/s, the particle size in a state immediately after the occurrence of dew formation becomes different, as described hereinabove, from that in a state after 10 min have elapsed (these results are not shown in FIG. 7). Therefore, it is preferred that the air flow velocity be equal to or greater than 0.2 m/s. Meanwhile, where the air flow velocity is equal to or greater than 0.2 m/s, the dew formation particle size increases gradually with the increase in air flow velocity, although the variability tends to be somewhat unstable. Accordingly, it is clear that within a range of air flow velocity of equal to or higher than 0.2 m/s, the dew formation particle size can be controlled to the desired value with good stability by controlling the air flow velocity.

Figure 8:
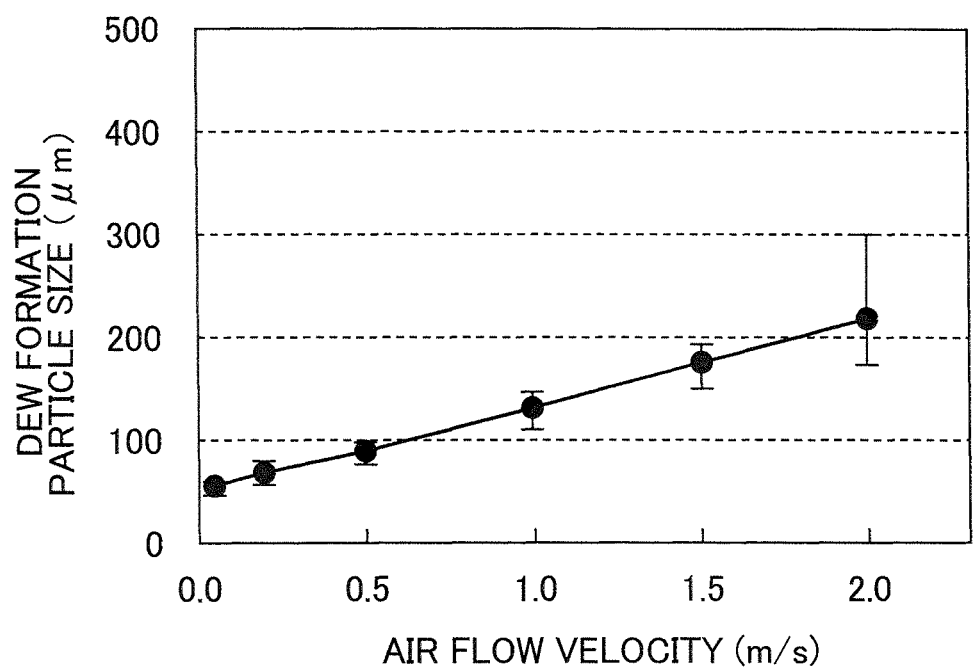
FIG. 8 is a characteristic diagram illustrating the relationship between the air flow velocity and the spread of particle size of dew formation (an example of results obtained in the case where the angle is 30 degrees).

When the air flow direction angle is 5 degrees, where the air flow velocity is 1.5 m/s, the variability increases, but when the air flow direction angle is 30 degrees, the variability is improved, as shown in FIG. 8. Further, it is clear that within a range of air flow velocity of less than 2.0 m/s, the particle size changes stably in response to variations in air flow velocity and the variability is also substantially stabilized. These results indicate that in order to generate uniform dew formation on the testing sample W, it is preferred that the air flow velocity be equal to or higher than 0.2 m/s and less than 2.0 m/s and that the air flow direction angle be 5 degrees to 30 degrees, preferably 10 degrees to 30 degrees.

The air flow velocity may be measured by providing an air flow velocity sensor 71, for example, at a position that is 20 mm above the testing sample W. Where the relationship between the rotation speed of the first fan 45 and the air flow velocity is determined, the air flow velocity sensor 71 can be removed.

Figure 9:
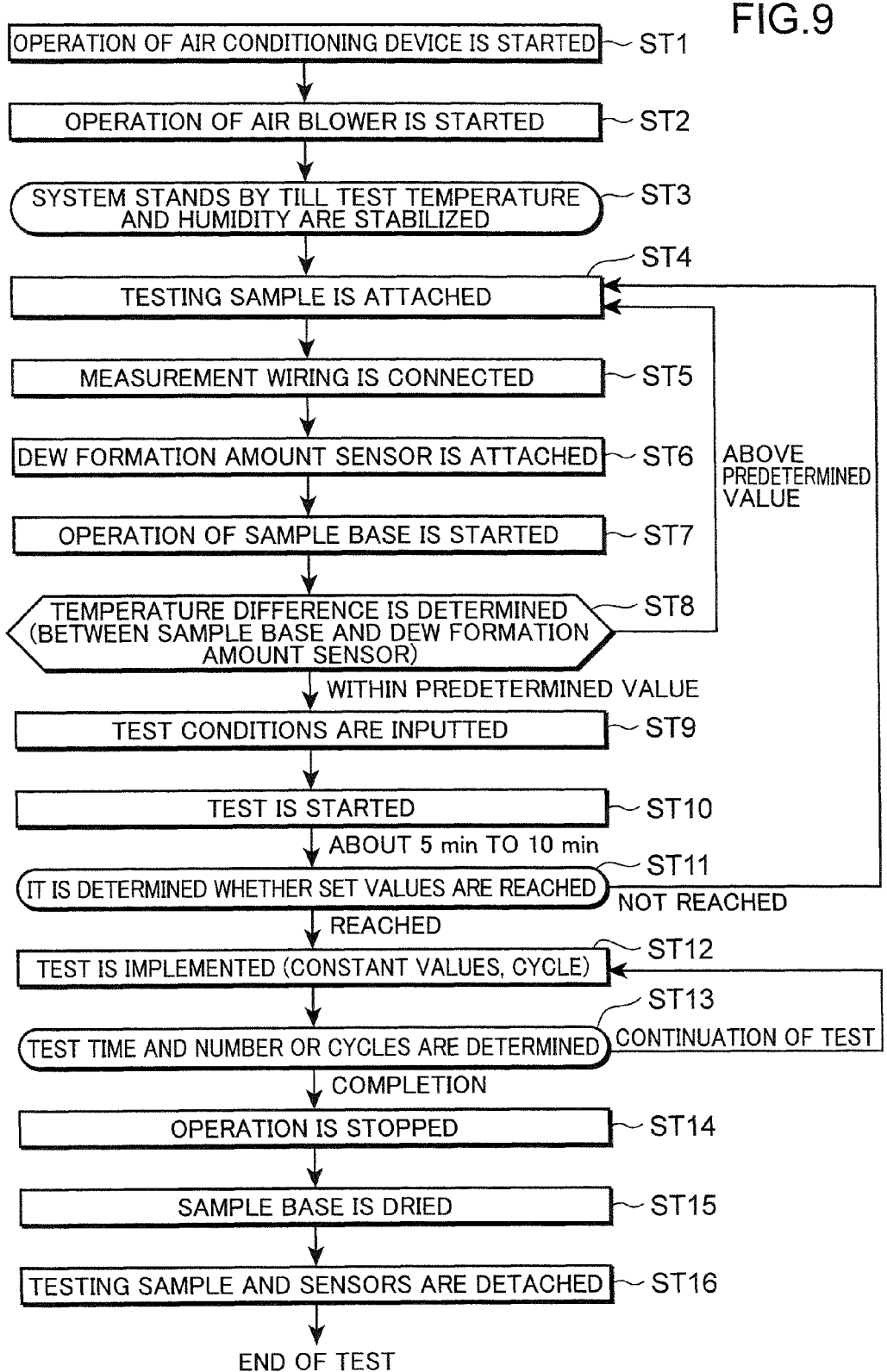
FIG. 9 is a flowchart illustrating the sequence of the dew formation testing method performed with the dew formation testing device.

The dew formation testing method performed with the dew formation testing device 10 of the present embodiment will be explained below with reference to FIG. 9. As shown in FIG. 9, first, the operation of the air conditioning device of the adjustment tank 12, that is, the humidifier 25 and the heater 29 (or the cooler 27) is started and the operation of the air blower 31 is started (steps ST1, 2). Then, the system stands by till the temperature and humidity of the upstream space SU become the test temperature and test humidity that have been set (step ST3). Within this period, the testing sample W is washed and dried. The test temperature and test humidity are, for example, 25° C., 50% RH, or 85° C., 85% RH.

Once the temperature and humidity inside the upstream space SU have reached the desired temperature and humidity, the lid 59 of the casing 35 of the testing tank 14 is opened and the testing sample W is attached to the sample base 43 (step ST4). When wiring to the testing sample W is required, as in the case where the testing sample W is an electronic device or the like, the measurement wiring is connected and the dew formation amount sensor 61 is attached to the testing sample W (steps ST5, 6). After the lid 59 has been closed, a voltage is applied to the Peltier element of the sample base 43 and the sample base 43 is cooled (step ST7). In this case, the Peltier element is controlled so that the temperature of the mounting surface 43*a* of the sample base 43 becomes a predetermined temperature (for example, 30° C.). Then, it is checked whether the difference in temperature between the mounting surface 43*a* of the sample base 43 and the dew formation amount sensor 61 corresponds to a predetermined value (step ST8). When the temperature difference is above the predetermined value, it can results from insufficiently tight attachment of the testing sample W or the dew formation amount sensor 61. In some cases, the testing sample W is temporarily removed and the step ST4 and subsequent steps are repeated as necessary. A temperature sensor (not shown in the figure) is attached to either of the sample base 43 and the dew formation amount sensor 61, and the aforementioned check is performed on the basis of measurement values obtained with the temperature sensors. For example, a temperature difference of 2° C. can be taken as the predetermined value.

Where the temperature difference is equal to or less than the predetermined value, a conclusion is made that the testing sample W is smartly attached to the sample base 43 and that the dew formation amount sensor 61 is smartly attached to the testing sample W. Accordingly, test conditions are then inputted (step ST9). The inputted test conditions include the dew formation amount, number of cycles, test time, and the like. Where a command to start the test is inputted (step ST10), the revolution speed of the first fan 45 and the temperature of the sample base 43 are controlled to obtain the preset dew formation amount. In this case, whether or not the dew formation test is performed so that the set conditions are satisfied is checked by checking the dew formation amount after a predetermined time interval has elapsed (for example, about 5 min to 10 min) (step ST11). When the predetermined dew formation amount is not demonstrated, it can be caused by disconnection of wiring. Therefore, rechecking is performed. Where the predetermined dew formation amount is demonstrated, the test is continued (step ST12).

In the dew formation test in which dew formation is caused on the testing sample W, the humidifier 25, the heater 29, and the air blower 31 are driven and, if necessary, the cooler 27 is driven in the adjustment tank 12. Therefore, the air with the temperature and humidity adjusted to the predetermined temperature and humidity circulates between the buffer space SB and the adjustment space SA. Part of the air with the predetermined temperature and predetermined humidity is caused by the first fan 45 to flow from the buffer space SB into the upstream duct 17 and guided into the testing tank 14. Thus, the air located inside the buffer space SB flows out correspondingly to the revolution speed of the first fan 45 and is introduced into the testing tank 14. For this reason, even if the amount of air flow (air flow velocity) created by the air blower 31 fluctuates, the effect of velocity fluctuations of the air flow created by the air blower 31 can be reduced inside the testing tank 14 and therefore the flow velocity of the air adjusted to the predetermined temperature and humidity can be stabilized inside the testing tank 14.

In the testing tank 14, the air that has passed the first fan 45 and between the flow adjusting plates 47 is guided by the tilted portion 38*b* of the casting 35 and flows downward at a predetermined tilting angle with respect to the horizontal direction. This air is then cooled by the mounting surface 43*a* of the sample base 43 and the surface of the testing sample W. In this case, moisture contained in the air condensates on the mounting surface 43*a* or on the testing sample W. The flow velocity of air causing dew formation on the testing sample W is within a range of 0.2 m/s to 2.0 m/s and the direction of air flowing toward the testing sample W in the vicinity of the testing sample W is at an angle of 5 degrees to 80 degrees. Therefore, substantially uniform dew formation can be created over the entire surface of the testing sample W and such uniform dew formation can be maintained for a long time.

The air that has passed above the sample base 43 passes through a gap between the partition member 41 and the opposing side wall 37*b* of the casing 35, flows into the downstream space SD, and then passes through the second fan 49 and between the fins 51. In this case, since the fins 51 receive heat of the heat emitting portion of the Peltier element and are heated, the air passing therebetween is heated by the fins 51. Therefore, moisture contained in the air is prevented from condensation inside the downstream space SD. This air passes through the downstream duct 18 and returns into the adjustment tank 12. Such circulation of air is repeated during the dew formation test.

The dew formation test includes a constant value test and a cycle test. The constant value test is a test in which the revolution speed of the first fan 45 and the temperature of the sample base 43 are adjusted and maintained over a preset test time so as to obtain a preset dew formation amount. In other words, the constant value test is a test in which only a dew formation process is executed. By contrast, in the cycle test, the dew formation amount, dew formation time, drying time, and number of cycles are set, and the dew formation step and drying step are repeated a predetermined number of times. Steps ST12, 13 are implemented as appropriate, depending on whether the constant value test or the cycle test is realized, the operation is stopped when the test is completed (step ST14).

Finally, the operation of heating the sample base 43 is performed (step ST15) and the sample base 43 is dried. Once the drying operation has been completed, the lid 59 of the casing 35 is opened, the measurement wiring, dew formation amount sensor 61, and testing sample W are removed, and the test is completed (step ST16).

The dew formation testing device 10 of the present embodiment is an environment testing device in which constant-temperature and constant-humidity testing can be performed. In constant-temperature and constant-humidity testing, control is performed to maintain the temperature and humidity inside the upstream space SU at the preset temperature and humidity (for example, 85° C., 85% RH). In this test, it is not necessary to cause dew formation on the surface of the testing sample W. Therefore, the air conditioning devices (the humidifier 25, the cooler 27, the heater 29, and the air blower 31) are driven without cooling the sample base 43. Thus, a moisture resistance stress can be applied separately from the dew formation testing in a state in which the testing sample W remains set on the sample base 43. Thus, in the dew formation testing device 10 of the present embodiment, not only the dew formation test, but also the moisture resistance test can be performed without removing the testing sample W from the testing space ST.

As explained hereinabove, in the testing device 10 according to the first embodiment, dew formation is caused on the surface of the testing sample W by cooling the testing sample W by means of cooling the mounting surface 43a of the sample base 43. Further, the air guide member 57 is provided that guides the air in the direction tilted downward at the predetermined angle, the guidance being performed at a position right above the end of the sample base 43 which is on the upstream side of the air flow. Therefore, the adjusted air introduced into the testing tank 14 can flow toward the testing sample W at the predetermined angle. For this reason, the air can uniformly fall on the testing sample W over the range from the upstream side of the air flow to the downstream side of the air flow. As a consequence, the particle size of dew formation generated on the surface of the testing sample W can be stabilized. Furthermore, since the air that has flown into the testing tank 14 flows on the sample base 43 from a side of the sample base 43, even when water of condensation that has been generated inside the upstream duct 17 drops down from the outlet port of the duct 17, this water does not fall on the sample base 43 or the testing sample W. Therefore, water of condensation generated inside the duct 17 can be prevented from affecting the dew formation on the testing sample W. Furthermore, because of a configuration in which the testing tank 14 is installed separately from the adjustment tank 12 and the two are linked by the ducts 17, 18, vibrations generated in the adjustment tank 12 can be prevented from being transmitted to the testing tank 14. As a result, the effect on dew formation occurring on the surface of the testing sample W placed on the sample base 43 can be inhibited. Because of the synergism of these effects, small-diameter dew formation can be generated with good stability. Therefore, the dew formation on the testing sample W can be maintained in a substantially uniform state.

In the first embodiment, the upstream end of the upstream duct 17 is provided at a position lower than the downstream end. Therefore, water of condensation generated inside the upstream duct 17 can be prevented from flowing into the testing tank 14 even without providing additionally a member for preventing the water of condensation from flowing into the testing tank 14. Further, water droplets floating in the air can be prevented from being introduced into the testing tank 14 through the upstream duct 17 and falling on the testing sample surface.

Further, in the first embodiment, since the air flow velocity is 0.2 m/s to 2 m/s and the tilting angle of the air guide member 57 is 5 degrees to 80 degrees with respect to the horizontal direction, the dew formation on the testing sample W can be maintained in a substantially uniform state more effectively. In other words, where the air flow velocity is equal to or greater than 0.2 m/s, the dew formation can be stabilized over the predetermined elapsed time, and where the air flow velocity is less than 2.0 m/s, variability in the particle size of dew can be inhibited. When the air flow direction is 0 degree with respect to the horizontal direction, the thickness of the layer in which the air does not flow increases with a transition toward the downstream side of the air flow. As a result, heat exchange with the surface of the testing sample W is inhibited and the particle size of dew tends to increase on the downstream side of the air flow. By contrast, when the air flow direction is 90 degrees (perpendicular) with respect to the horizontal direction, a stagnation point appears. Therefore, heat exchange with the surface of the testing sample W is inhibited, the particle size of dew tends to increase in a substantially central portion and an entirely turbulent flow is generated downstream of the stagnation point. As a result, particle size is destabilized. Therefore, dew formation can be stabilized in a substantially uniform state by setting the air flow velocity to 0.2 m/s to 2.0 m/s and the inclination of the air guide member 57 to 5 degrees to 80 degrees.

In the first embodiment, the buffer space SB is formed inside the adjustment tank 12 and the air located inside the buffer space SB is introduced into the testing tank 14. Since the flow velocity and humidity distribution of the air flowing out of the buffer space SB are stable, the flow velocity and humidity distribution of the air flowing toward the testing sample W is stabilized. As a result, dew formation on the testing sample W can be maintained in a substantially uniform state more effectively.

In the first embodiment, the surface area of the air flow channel from the upstream side of the air flow toward the downstream side of the air flow decreases gradually in the upstream space SU. Therefore, the direction of air flow can be easily restricted. As a result, the flow of the air flowing on the testing sample W can be stabilized and dew formation on the testing sample W can be maintained in a substantially uniform state more effectively.

In the first embodiment, part of the casing 35 is caused to function as the air guide member 57. Therefore, the air guiding effect can be obtained without adding a member to the casing 35 of the testing tank 14.

In the first embodiment, the dew formation amount sensor 61 is provided. Therefore, the state of dew formation on the surface of the testing sample W can be clarified.

In the first embodiment, the thermal resistance reducing material 55 is provided on the mounting surface 43a of the sample base 43. Therefore, heat of the sample base 43 can be easily transmitted to the testing sample W and variability in a heat conduction amount can be inhibited. Therefore, the adjustment of the dew formation state on the testing sample W can be easily conducted more accurately. Further, the testing sample can be brought into intimate contact with the mounting surface 43a of the sample base 43 even when the contact surface of the testing sample W is not flat.

In the first embodiment, the sample base 43 is configured to have a Peltier element. Therefore, the dew formation state on the testing sample W can be adjusted by controlling the voltage applied to the Peltier element. Further, since the air that has passed above the testing sample W is heated by the heat emitted from the Peltier element, the unnecessary condensation inside the testing tank 14 can be inhibited without adding a new heater. Thus, since the air passing above the testing sample W is cooled, the relative humidity thereof increases. Therefore, condensation inside the testing tank 14 is facilitated. However, since the air with increased relative humidity is heated by the heat emitting portion of the Peltier element, condensation inside the testing tank 14 can be inhibited.

In the first embodiment, the dew formation testing device 10 is of a system such that the air is circulated between the adjustment tank 12 and the testing tank 14, but such a configuration is not limiting. Thus, it is possible to remove the downstream duct 18 and suck in the external air from the inflow port 21c of the adjustment tank 12. In this case, the air that has cooled the testing sample W inside the testing tank 14 is discharged to the outside through the lead-out port 37d. With such a configuration, it is not necessary to form the lead-out port 37d of the testing tank 14 in the same side wall 37a as the introducing port 37c, and the lead-out port 37d may be formed, for example, in the opposing side wall 37b.

Figure 10:
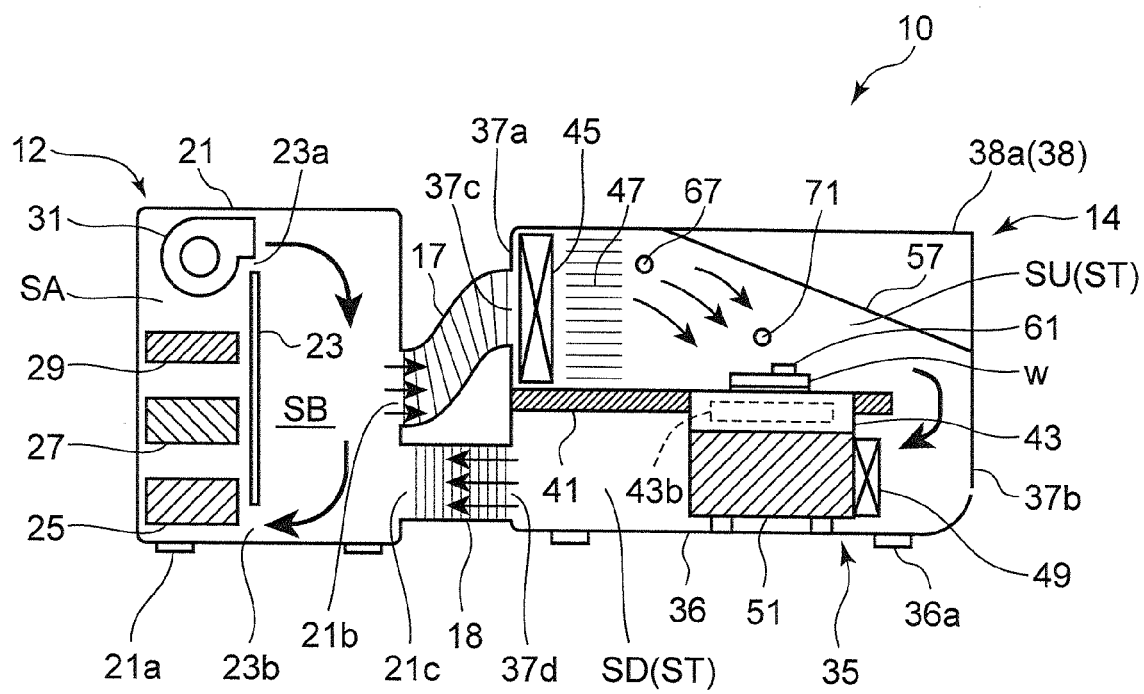
FIG. 10 illustrates schematically the dew formation testing device according to the variation example of the first embodiment of the present invention.

Further, in the first embodiment, part (tilted portion 38b) of the casing 35 functions as the air guide member 57, but such a configuration is not limiting. For example, the air guide member 57 may be provided on the inside of the casing 35, as shown in FIG. 10. FIG. 10 illustrates the configuration example in which the air guide member 57 is fixed to the ceiling 38 and the side wall 37b of the casing 35. However, the air guide member 57 may be attached to the casing 35 so that the tilting angle could be changed. For example, where the upper end of the air guide member 57 is rotatably joined to the ceiling 38 of the casing 35, the inclination of the air guide member 57 can be changed. Accordingly, the dew formation state on the surface of the testing sample W can be adjusted by changing the angle of the air guide member 57.

Figure 11:
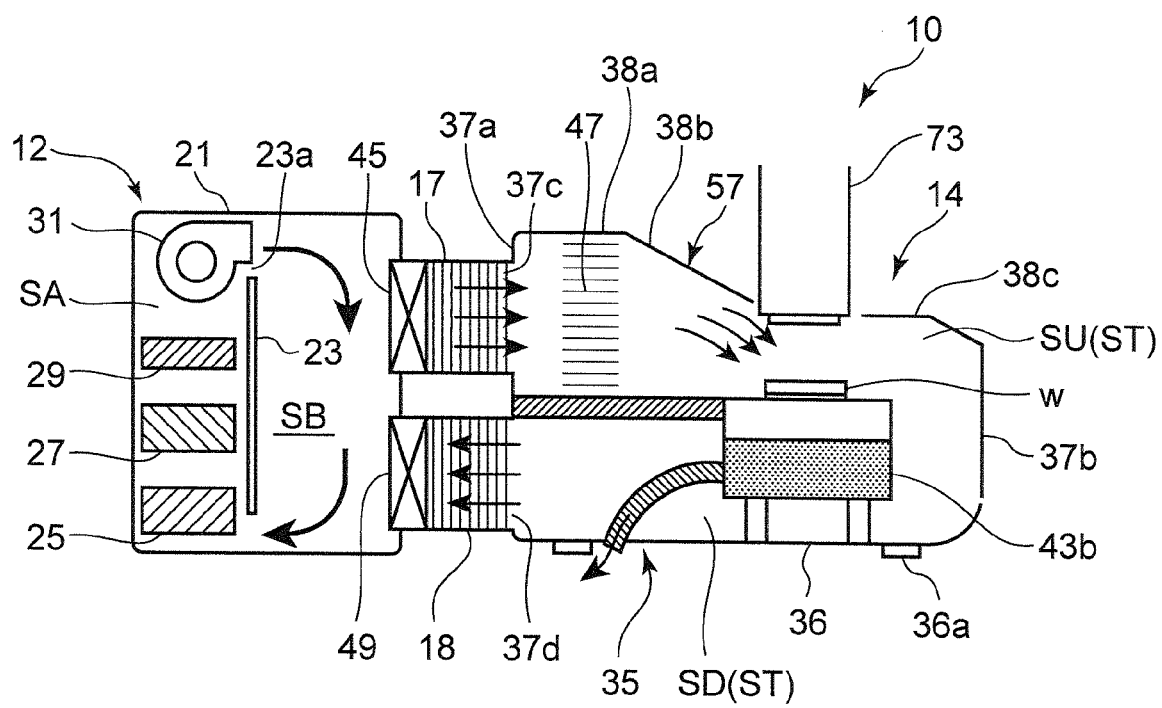
FIG. 11 illustrates schematically the dew formation testing device according to the variation example of the first embodiment of the present invention.

As shown in FIG. 11, the dew formation testing device 10 may be provided with a microscope 73. In the configuration shown in FIG. 11, the ceiling 38 of the casing 35 is provided with the horizontal portion 38a, the tilted portion 38b continuing from the horizontal portion 38a, and an extending portion 38c that extends sidewise from the lower end of the tilted portion 38b. The tilted portion 38b extends upward of the sample base 43 toward the opposing side wall 37b from a location on the upstream side of the sample base 43. In other words, the tilted portion 38b passes through the position right above the sample base 43 at an end thereof which is on the upstream side of the air flow and extends from the upstream side of the air flow to the downstream side of the air flow. However, by contrast with the first embodiment, the tilted portion 38b does not reach the position right above the sample base 43 at an end thereof which is on the downstream side of the air flow. The tilted portion 38b functions as the air guide member 57 in the same manner as in the first embodiment. A microscope 73 is provided at a position right above the vicinity of the center of the sample base 43. The lower end of the microscope 73 is introduced into the upstream space SU through the opening formed in the extending portion 38c, but is unlikely to hinder the flow of air guided by the tilted portion 38b. In this variation example, fine dew formation state on the testing sample W can be observed. Furthermore, since the microscope 73 is positioned at the extending portion 38c that is connected to the air guide member 57 and extends therefrom in the horizontal direction, the microscope 73 can be prevented from perturbing the flow of air.

The heating-cooling unit 43b is not limited to the configuration having a Peltier element. For example, the heating-cooling unit 43b may be configured so that cooling water can be introduced from a chiller (not shown in the figure), as shown in FIG. 11. In a case where the air is heated in the downstream space SD, a heater (not shown in figures) may be provided in the passage of the air, although the provision of a heater may be omitted.

This modification of the heating-cooling unit 43b may be adapted to the second embodiment and other modifications.

Further, the upstream duct 17 may be formed so as to be folded in a U-like shape such that the intermediate portion thereof positioned down. With such a configuration, even if the outflow port 21b of the adjustment tank 12 and the introducing port 37c of the testing tank 14 are formed at a substantially same height, moisture that has condensed inside the upstream duct 17 will remain inside the upstream duct 17 and can be prevented from flowing into the testing tank 14.

Second Embodiment

Figure 12:
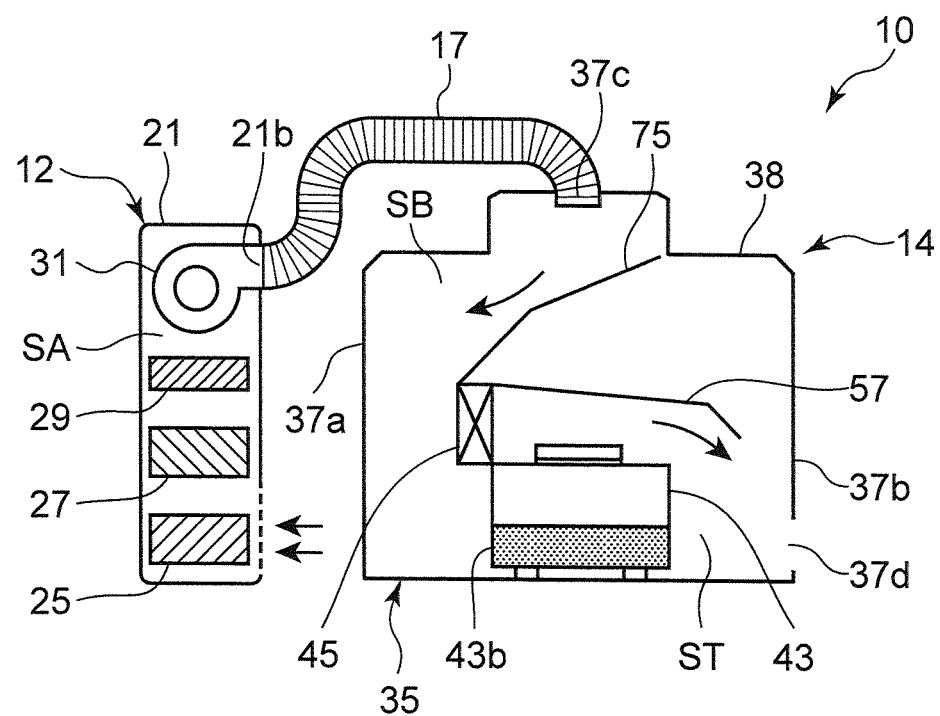
FIG. 12 illustrates schematically the dew formation testing device according to the second embodiment of the present invention.

FIG. 12 illustrates the second embodiment of the present invention. In the second embodiment, by contrast with the first embodiment, the buffer space SB is formed inside the testing tank 14. In this case, constituent elements identical to those of the first embodiment are assigned with like reference numerals and symbols and detailed explanation thereof is herein omitted.

In the second embodiment, the partition plate 23 is not provided inside the adjustment tank 12, and the space inside the adjustment tank 12 is constituted as the adjustment space SA. The outflow port 21b and the inflow port 21c are formed in the casing 21 of the adjustment tank 12 so as to face the adjustment space SA. The upstream duct 17 is attached to the outflow port 21b, and the air blown out from the air blower 31 flows directly into the upstream duct 17. The inflow port 21c introduces the external air into the adjustment space SA.

A partition plate 75 is provided inside the testing tank 14. The space inside the testing tank 14 is partitioned into the buffer space SB and the testing space ST by the partition plate 75, the sample base 43, and the heating-cooling unit 43b. The introducing port 37c of the casing 35 is formed in the ceiling 38 and faces the buffer space SB. Therefore, the air that has flown through the upstream duct 17 initially flows into the buffer space SB. In this case, the air flows downward. The introducing port 37c may be formed in the side wall 37a, rather than in the ceiling 38. In this case, it is preferred that the position of the introducing port 37c be shifted in the height direction or sidewise with respect to the position of the below-described communication portion (communication portion between the buffer space SB and the testing space ST). As a result, the air that has flown out of the upstream duct 17 can be prevented from flowing directly into the testing space ST.

The first fan 45 is provided in the communication portion through which the buffer space SB communicates with the testing space ST. Therefore, the air located inside the buffer space SB flows through the first fan 45 into the testing space ST. The lead-out port 37d faces the testing space ST. The first fan 45 may be also provided inside the buffer space SB or inside the testing space ST, instead of the communication portion.

The air guide member 57 is provided inside the testing space ST and connected to the lower end of the partition plate 75. Further, the air guide member 57 is disposed obliquely so as to descend gradually with a transition from the upstream side of the air flow to the downstream side of the air flow. The lead-out port 37d is open in the opposing side wall 37b on the side opposite that of the buffer space SB, and the air that has flown through inside the testing space ST is discharged to the outside through the lead-out port 37d. The dew formation testing device 10 according to the second embodiment may be also of a circulation system in which the air located inside the testing tank 14 is returned to the adjustment tank 12. In this case, it is possible to form the inflow port 21c in the adjustment tank 12 and connect the inflow port 21c to the lead-out port 37d of the testing tank 14 by the downstream duct 18 (see FIG. 13).

Other features, operation, and effect are similar to those of the first embodiment and the explanation thereof is herein omitted.

Figure 13:
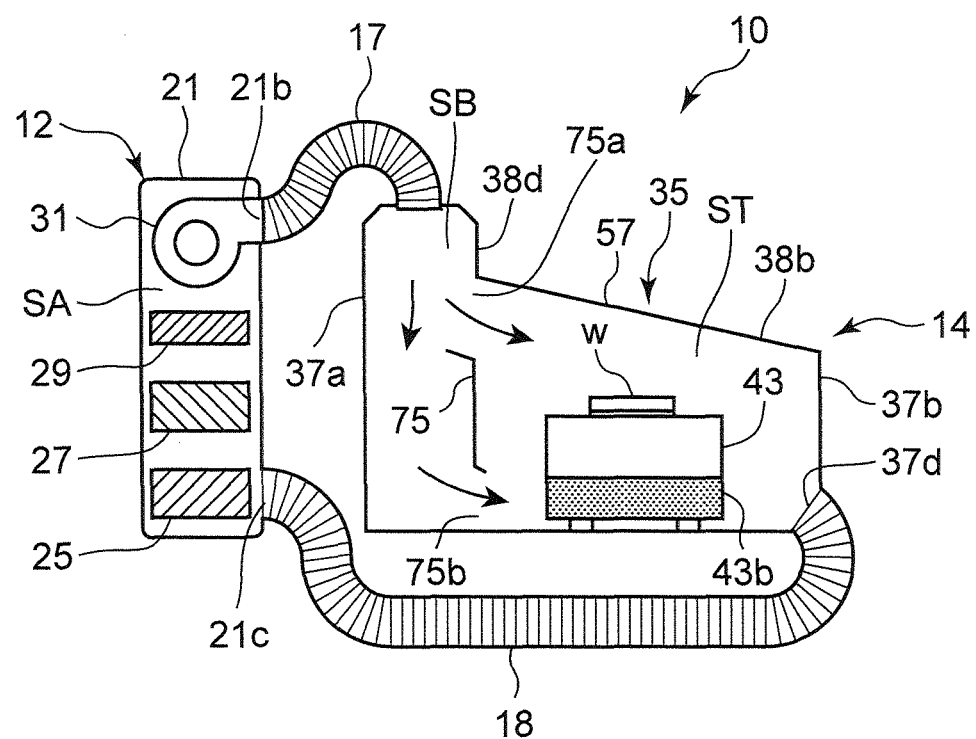
FIG. 13 illustrates schematically the dew formation testing device according to the variation example of the second embodiment of the present invention.

As shown in FIG. 13, the air guide member 57 may be configured as part of the casing 35. Specifically, the ceiling 38 of the testing tank 14 is provided with a protruding portion 38d that is shaped to protrude upward and the tilted portion 38b. The tilted portion 38b extends obliquely downward from a part of connection to the protruding portion 38d and functions as the air guide member 57 in the same manner as in the first embodiment. The partition plate 75 is provided so as to extend in the vertical direction at a position right below the vicinity of the connection portion of the protruding portion 38d and the tilted portion 38b of the ceiling 38. Communication holes 75a, 75b are formed in the upper end portion and the lower end portion of the partition plate 75, and the air introduced into the buffer spaced SB flows through the communication holes 75a, 75b into the testing space ST. The air that has flown into the testing space ST through the lower communication hole 75b cools the heat emitting portion of the Peltier element. The inflow port 21c is formed in the adjustment tank 12, and the inflow port 21c communicates with the lead-out port 37d of the testing tank 14 via the downstream duct 18. A configuration in which the partition plate 75 is constituted by a plate material in which a large number of holes or slits are formed over substantially the entire surface, as in the punching metal or the like, may be used instead of the configuration in which the communication hole 75a is formed in the upper end portion and the lower end portion of the partition plate 75.

Figure 14:
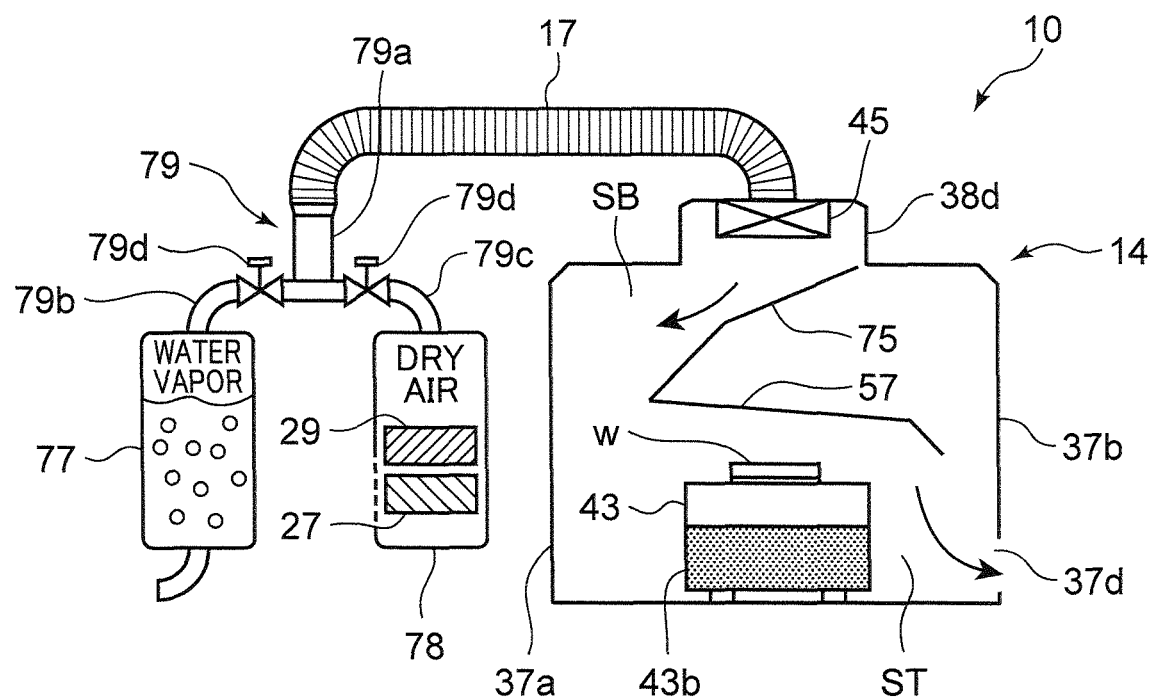
FIG. 14 illustrates schematically the dew formation testing device according to the variation example of the second embodiment of the present invention.

In the second embodiment, the example is explained in which the adjustment unit is constituted by the adjustment tank 12 provided with the humidifier 25, the cooler 27, the heater 29, and the air blower 31, but such a configuration is not limiting. For example, as shown in FIG. 14, the adjustment unit that can adjust the temperature and humidity of air to the predetermined temperature and humidity may be provided with a bubbler 77 that generates humidified air by using a typical divided flow method, a dry air generation unit 78 that generates dry air, and a pipe 79 connecting the bubbler 77 and the dry air generation unit 78 to the upstream duct 17. In this case, the bubbler 77 and the dry air generation unit 78 are provided in respective housings and configured separately from each other. In the dry air generation unit 78, the heater 29 and the cooler 27 are provided inside the housing and connected to the dry air source (not shown in the figure). The pipe 79 is provided with a main pipe 79a, a first branch pipe 79b that is branched off from the main pipe 79a and connected to the bubbler 77, and a second branch pipe 79c that is branched off from the main pipe 79a and connected to the dry air generation unit 78. A flow rate regulating valve 79d is provided in either of the first branch pipe 79b and the second branch pipe 79c, the flow rate of humidified air and dry air can be regulated. FIG. 14 shows the configuration in which the humidified air is generated by the divided flow method, but for example a two-temperature method or another humidity generating method can be selected as appropriate instead of the divided flow method.

A test has been conducted to verify the reproducibility of dew formation produced with the dew formation testing device 10 of each of the abovementioned embodiments. An example of the results will be explained below. In the test, a glass epoxy substrate with a silver plated electrode formed thereon was used as the testing sample W, and a cyclic test was conducted in which the dew formation step and the drying step were repeated in a state in which a voltage of 25 V was applied between the electrodes. The dew formation step took 20 min and the drying step took 10 min. The time before each of the testing samples W was determined to fail was recorded. The failure determination criterion in this case was whether or not the insulation resistance value between the electrodes became equal to or less than 1 MΩ.

Figure 15:
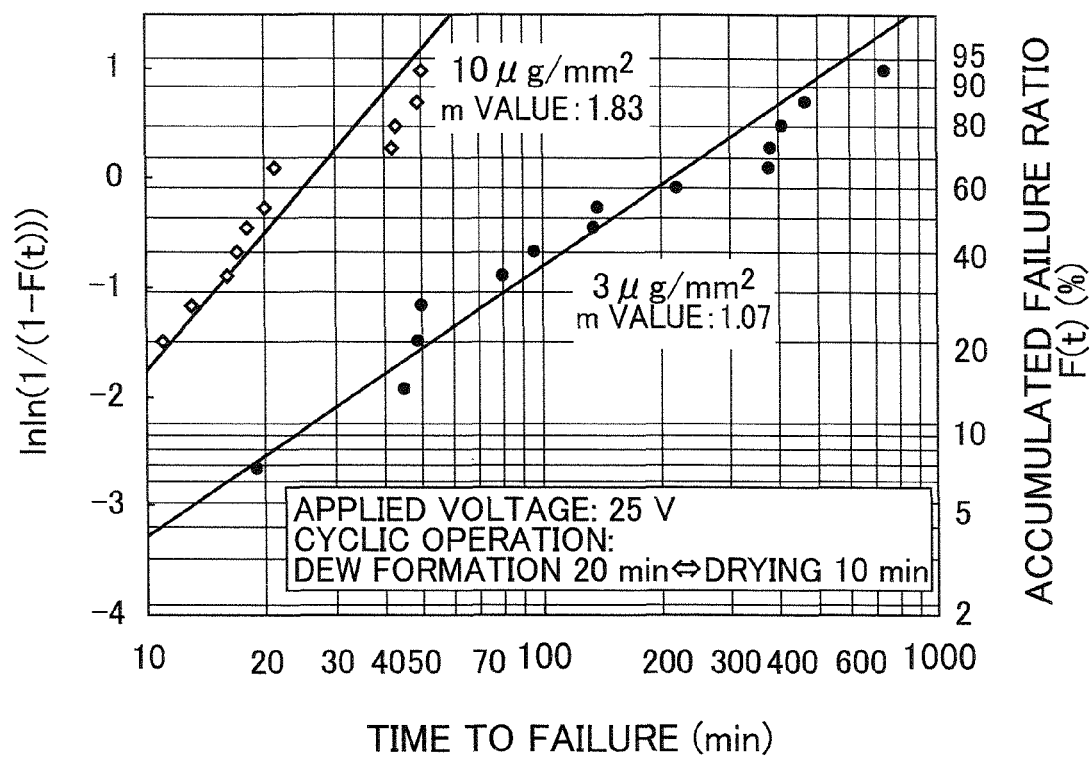
FIG. 15 is a characteristic diagram illustrating an example of test results for reproducibility verification by using a Weibull plot.

FIG. 15 shows the results obtained with the testing device 10 shown in FIG. 12 in the case where the set value of dew formation amount was changed variously. In FIG. 15, a failure occurrence time is plotted against the abscissa, and an accumulated failure ratio and a ln {ln 1/(1−F(t))} represented as Weibull plot are plotted against the ordinates. The solid line in the figure relates to the case where the set value of the dew formation amount is 3 μg/mm², and the broken line relates to the case where the set value of the dew formation amount is 10 μg/mm². The m value, which is the shape parameter, was 1.07 and 1.83, respectively. Since the shape parameter was higher than 1, the device is found to be effective as an accelerated life testing device of a wear failure type.

Summary of the Embodiments

The aforementioned embodiments are summarized below.

(1) In the aforementioned embodiments, dew formation is caused on the surface of the testing sample by cooling the testing sample by means of cooling the mounting surface of the sample base. Further, the air guide member is provided that guides the air in the direction tilted downward at a predetermined angle, the guidance being performed at a position right above the end of the sample base which is on the upstream side of the air flow. Therefore, the adjusted air introduced into the testing tank can flow toward the testing sample at the predetermined angle. For this reason, the air can uniformly fall on the testing sample over the range from the upstream side of the air flow to the downstream side of the air flow. As a consequence, the particle size of dew formation generated on the surface of the testing sample can be stabilized. Furthermore, since the air that has flown into the testing tank flows on the sample base from a side of the sample base, even when water of condensation that has been generated inside the duct drops down from the outlet port of the duct, this water does not fall on the sample base or the testing sample. Therefore, water of condensation generated inside the duct can be prevented from affecting the dew formation on the testing sample. Furthermore, because of a configuration in which the testing tank is installed separately from the adjustment unit and the two are linked by the duct, vibrations generated in the adjustment unit can be prevented from being transmitted to the testing tank. As a result, the effect on dew formation occurring on the surface of the testing sample placed on the sample base can be inhibited. Because of the synergism of these effects, small-diameter dew formation can be generated with good stability. Therefore, the dew formation on the testing sample can be maintained in a substantially uniform state.

(2) The upstream end of the duct may be provided at a position lower than the downstream end. With such a configuration, water of condensation generated inside the duct can be prevented from flowing into the testing tank even without providing additionally a member for preventing the water of condensation from flowing into the testing tank. Further, water droplets floating in the air can be prevented from being introduced into the testing tank through the duct and falling on the testing sample surface.

(3) It is preferred that the flow velocity of air flowing from the side of the sample base toward the sample base be 0.2 m/s to 2 m/s. In such a case, the dew formation on the testing sample can be maintained in a substantially uniform state more effectively.

(4) It is preferred that the tilting angle of the air guide member at a position right above the sample base at the end thereof which is on the upstream side of the air flow be 5 degrees to 80 degrees with respect to the horizontal direction.

In such a case, the dew formation on the testing sample can be maintained in a substantially uniform state more effectively.

It is preferred that a buffer space be formed that stabilizes the flow velocity of the air adjusted to predetermined temperature and humidity. In such a case, the flow velocity of the air flowing out of the buffer space is stabilized and therefore the flow velocity of the air flowing toward the testing sample is stabilized. As a result, the dew formation on the testing sample can be maintained in a substantially uniform state more effectively.

(6) It is preferred that the air guide member decrease the area of the air flow passage from the upstream side of the air flow toward the downstream side of the air flow. In such a case, the area of the air flow passage decreases gradually from the upstream side of the air flow toward the downstream side of the air flow. This makes it easier to regulate the direction of air flow. As a result, the flow of the air flowing on the testing sample can be stabilized and dew formation on the testing sample can be maintained in a substantially uniform state more effectively.

(7) The air guide member may be part of the casing of the testing tank. With such a configuration, the air guiding effect can be obtained without adding a member to the casing of the testing tank.

(8) The testing tank may be provided with a microscope capable of magnifying the surface of the testing sample. With such a configuration, the state of fine dew formation on the testing sample can be observed.

(9) The testing tank is preferably provided with a dew formation detection unit that can detect dew formation occurring on the surface of the testing sample. With such a configuration, the state of dew formation on the surface of the testing sample can be clarified.

(10) At least one of the flow velocity of the air and the angle of the air guide member may be variable. With such a configuration, the state of dew formation on the surface of the testing sample can be adjusted by changing at least either of the flow velocity of the air and the angle of the air guide member.

(11) A thermal resistance reducing material may be provided on the mounting surface of the sample base. With such a configuration, heat of the sample base can be easily transmitted to the testing sample and the spread in a heat conduction amount can be inhibited. Therefore, the adjustment of the dew formation state on the testing sample can be easily conducted more accurately. Further, the testing sample can be brought into intimate contact with the mounting surface of the sample base even when the contact surface of the testing sample is not flat.

(12) The sample base may have a Peltier element. With such a configuration, the dew formation state on the testing sample can be adjusted by controlling the voltage applied to the Peltier element.

(13) The air that has passed over the testing sample may be heated by the heat emitted from the Peltier element. With such a configuration, the unnecessary condensation inside the testing tank can be inhibited without adding a new heater. Thus, since the air passing above the testing sample is cooled, the relative humidity thereof increases. Therefore, condensation inside the testing tank is facilitated. However, since the air with increased relative humidity is heated by the heat emitting portion of the Peltier element, condensation inside the testing tank can be inhibited.

(14) The dew formation testing method according to the aforementioned embodiment includes: adjusting the temperature and humidity of air to predetermined temperature and humidity inside the adjustment unit; introducing the air from the adjustment unit into the testing tank through the duct; cooling the mounting surface of the sample base, onto which the testing sample has been placed, inside the testing tank; and guiding the air from a side of the sample base in a direction tilted downward at a predetermined angle, with the guidance being performed at a position right above the sample base at an end thereof which is on the upstream side of the air flow, and causing the air to flow on the sample base, thereby causing dew formation on the testing sample.

(15) In the aforementioned dew formation testing method, it is preferred that the air be caused to flow from the side of the sample base toward the sample base at a flow velocity of 0.2 m/s to 2 m/s.

(16) In the aforementioned dew formation testing method, it is preferred that the air be caused to flow obliquely downward at an angle of 5 degrees to 80 degrees with respect to the horizontal direction from the side of the sample base toward the sample base.

(17) In the aforementioned dew formation testing method, it is preferred that the flow velocity and humidity distribution of the air inside the buffer space be stabilized and the air having the stabilized flow velocity and humidity distribution be caused to flow obliquely downward from the side of the sample base onto the sample base.

The invention claimed is:

1. A dew formation testing device for performing dew formation testing, the device comprising:
    an adjustment unit having a casing in which the adjustment unit adjusts temperature and humidity of air to predetermined temperature and humidity;
    a testing tank having a casing installed at a place separated from a place where the casing of the adjustment unit is installed, wherein the casing of the testing tank houses a sample base that has a mounting surface, onto which a testing sample can be placed, and that is capable to cool the mounting surface; and
    a duct linking the casing of the adjustment unit and the casing of the testing tank so as not transmit vibration of the casing of the adjustment unit to the testing tank, wherein
    the testing tank is provided with an air guide member that, when air flowing into the testing tank through the duct flows onto the sample base from a side of the sample base, guides the air in a direction tilted downward at a predetermined angle, the guidance being performed at a position right above the sample base at an end thereof which is on the upstream side of the air flow, the air guide member decreasing an area of an air flow passage from the upstream side of the air flow toward the downstream side of the air flow.

2. The dew formation testing device according to claim 1, wherein an upstream end of the duct is provided at a position lower than a downstream end thereof.

3. The dew formation testing device according to claim 1, wherein a flow velocity of air flowing from the side of the sample base toward the sample base is 0.2 m/s to 2 m/s.

4. The dew formation testing device according to claim 1, wherein
    a tilting angle of the air guide member at a position right above the sample base at the end thereof which is on the upstream side of the air flow is 5 degrees to 80 degrees with respect to the horizontal direction.

5. The dew formation testing device according to claim 1, wherein a buffer space is formed that stabilizes a flow velocity of the air adjusted to predetermined temperature and humidity.

6. The dew formation testing device according to claim 1, wherein the air guide member is part of a casing of the testing tank.

7. The dew formation testing device according to claim 1, wherein the testing tank is provided with a microscope capable of magnifying a surface of the testing sample.

8. The dew formation testing device according to claim 1, wherein at least one of the flow velocity of the air and the angle of the air guide member is variable.

9. The dew formation testing device according to claim 1, wherein the sample base has a Peltier element.

10. The dew formation testing device according to claim 9, wherein the air that has passed over the testing sample is heated by heat emitted from the Peltier element.

11. A dew formation testing for performing dew formation testing, the device comprising:
- an adjustment unit capable of adjusting temperature and humidity of air to predetermined temperature and humidity;
- a testing tank installed separately from the adjustment unit and provided with a sample base that has a mounting surface, onto which a testing sample can be placed, and that is capable to cool the mounting surface; and
- a duct linking the adjustment unit and the testing tank, wherein
- the testing tank is provided with an air guide member that, when air flowing into the testing tank through the duct flows onto the sample base from a side of the sample base, guides the air in a direction tilted downward at a predetermined angle, the guidance being performed at a position right above the sample base at an end thereof is on the upstream side of the air flow, and
- the testing tank is provided with a dew formation detection unit that can detect dew formation occurring on a surface of the testing sample.

12. A dew formation testing device for performing dew formation testing, the device comprising:
- an adjustment unit capable of adjusting temperature and humidity of air to predetermined temperature and humidity;
- a testing tank installed separately from the adjustment unit and provided with a sample base that has a mounting surface, onto which a testing sample can be placed, and that is capable to cool the mounting surface; and
- a duct linking the adjustment unit and the testing tank, wherein
- the testing tank is provided with an air guide member that, when air flowing into the testing tank through the duct flows onto the sample base from a side of the sample base, guides the air in a direction tilted downward at a predetermined angle, the guidance being performed at a position right above the sample base at an end thereof that is on the upstream side of the air flow, and
- a thermal resistance reducing material is provided on the mounting surface of the sample base.

* * * * *